(12) United States Patent
Hirota et al.

(10) Patent No.: US 8,778,408 B2
(45) Date of Patent: Jul. 15, 2014

(54) ANTIMICROBIAL SUBSTANCE, METHOD FOR PRODUCING SAME, AND ANTIMICROBIAL MATERIAL

(75) Inventors: Koji Hirota, Hayama-machi (JP); Hiroshi Mase, Iwakuni (JP)

(73) Assignee: Mitsui Chemicals, Inc., Minato-ku, Tokyo (JP)

( * ) Notice: Subject to any disclaimer, the term of this patent is extended or adjusted under 35 U.S.C. 154(b) by 0 days.

(21) Appl. No.: 13/985,816

(22) PCT Filed: Feb. 13, 2012

(86) PCT No.: PCT/JP2012/000934
§ 371 (c)(1),
(2), (4) Date: Aug. 15, 2013

(87) PCT Pub. No.: WO2012/111301
PCT Pub. Date: Aug. 23, 2012

(65) Prior Publication Data
US 2013/0323289 A1    Dec. 5, 2013

(30) Foreign Application Priority Data

Feb. 18, 2011  (JP) .................................. 2011-033669
Oct. 5, 2011   (JP) .................................. 2011-220978

(51) Int. Cl.
| | | |
|---|---|---|
| B32B 15/08 | (2006.01) | |
| B32B 15/12 | (2006.01) | |
| C23C 14/06 | (2006.01) | |
| C23C 14/24 | (2006.01) | |
| B32B 27/06 | (2006.01) | |
| B32B 29/06 | (2006.01) | |

(52) U.S. Cl.
USPC ........... 424/630; 424/400; 428/220; 428/389; 427/250; 442/123

(58) Field of Classification Search
CPC .............................. A01N 59/20; A01N 59/16
USPC ................................... 424/400, 630; 427/250
See application file for complete search history.

(56) References Cited

U.S. PATENT DOCUMENTS 4,009,947 A * 3/1977 Nishida et al. ................. 359/884
(Continued)

FOREIGN PATENT DOCUMENTS

| JP | 9-111378 A  | 4/1997 |
| JP | 10-110268 A | 4/1998 |

(Continued)

OTHER PUBLICATIONS

Beattie, Single Bath Electrodeposition of a Combinatorial Library of Binary Cu1—-xSnx Alloys; May 12, 2003; Journal of the Electrochemical Society; 150; vol. 7; whole document.*

(Continued)

*Primary Examiner* — Aaron Austin
*Assistant Examiner* — Tahseen N Khan
(74) *Attorney, Agent, or Firm* — Buchanan Ingersoll & Rooney PC (57) ABSTRACT

Provided an antimicrobial substance that includes a base material layer, and a copper-tin alloy layer 5-200 nm in thickness disposed on the base material layer, the copper-tin alloy layer containing copper in an amount of more than 60 atomic percent but not more than 90 atomic percent, and containing tin in an amount of not less than 10 atomic percent but less than 40 atomic percent. The copper-tin alloy layer includes a $Cu_{41}Sn_{11}$ crystalline phase, and a $Cu_3Sn$ crystalline phase. The Q value ($\Omega/(nm \cdot Cu$ atomic percent)), which is derived by dividing the sheet resistance ($\Omega$) of the copper-tin alloy layer by the thickness of the copper-tin alloy layer and the copper content (Cu atomic percent), is $1.5 \times 10^{-4}$-$6.0 \times 10^{-4}$.

15 Claims, 8 Drawing Sheets

(56) References Cited

U.S. PATENT DOCUMENTS

| | | | |
|---|---|---|---|
| 4,025,581 A * | 5/1977 | Powell et al. | 525/310 |
| 4,107,250 A * | 8/1978 | Zechinati et al. | 264/118 |
| 4,460,644 A * | 7/1984 | Pavlich | 428/314.4 |
| 5,770,255 A * | 6/1998 | Burrell et al. | 427/2.1 |
| 5,837,941 A * | 11/1998 | Tachikawa et al. | 174/125.1 |
| 6,565,913 B2 * | 5/2003 | Arps et al. | 427/2.24 |
| 2004/0043686 A1 * | 3/2004 | Batdorf | 442/123 |
| 2004/0224495 A1 * | 11/2004 | Young | 438/622 |
| 2005/0079987 A1 * | 4/2005 | Cartwright et al. | 510/296 |
| 2008/0090096 A1 * | 4/2008 | Suzuki et al. | 428/674 |
| 2008/0305153 A1 * | 12/2008 | Wang et al. | 424/443 |
| 2010/0015193 A1 | 1/2010 | Inaoka et al. | |
| 2010/0028823 A1 * | 2/2010 | Reid et al. | 433/6 |

FOREIGN PATENT DOCUMENTS

| | | | |
|---|---|---|---|
| JP | 2001-234468 A | | 8/2001 |
| JP | 2003171602 A * | | 6/2003 |
| JP | 2005226029 A * | | 8/2005 |
| JP | 2006-342418 A | | 12/2006 |
| JP | 2006342418 A * | | 12/2006 |
| JP | 3163574 U | | 10/2010 |
| JP | 3163575 U | | 10/2010 |
| JP | 3163576 U | | 10/2010 |
| WO | WO 2008/047810 A1 | | 4/2008 |

OTHER PUBLICATIONS

Grasser, M.; Thermodynamic Description of the System Cu—Sn—P Experimental and Numerical Investigation; Apr. 25, 2012; IJMR; whole document.*

Johnson, L.; Micoranalysis of Copper-Tin Phases in Dental Amalgam; Jun. 19, 1968; Department of Dental Materials at U. of Michigan; whole document.*

Machine_English_Translation_JP_2003171602a; Shimatani, H.; Jun. 20, 2003; JPO; whole document.*

Machine_English_Translation_JP_2005226029_A; Matsuoka, H.; Antibacterial Antidazzling Coating Material Composition, Aug. 25, 2005; whole document.*

Machine_English_Translation_JP_2006342418_A; Kanematsu, H.; Sn—Cu Alloy Thin Film Having Antibacterial Property; Dec. 21, 2006; whole document.*

13985816—EICSEARCH; STIC Search on Sheet Resistances; STN; Feb. 18, 2014; whole document.*

13985816-446586—EICSEARCH_2; STIC Search on Cu41Sn11 and Cu3Sn Films; STN; Feb. 18, 2014; whole document.*

International Search Report (PCT/ISA/210) issued on May 1, 2012, by the Japanese Patent Office as the International Searching Authority for International Application No. PCT/JP2012/000934.

* cited by examiner

ANTIMICROBIAL SUBSTANCE, METHOD FOR PRODUCING SAME, AND ANTIMICROBIAL MATERIAL

TECHNICAL FIELD

The present invention relates to antimicrobial raw materials, methods for producing the same, and antimicrobial materials.

BACKGROUND ART

To keep articles in a sanitary condition, antimicrobial substances are applied to their surface under certain circumstances. For example, in food-handling facilities, domestic kitchens and medical facilities, it is required to keep the surface of the interior floor and walls, instruments, fixtures or other articles germ-free in order to prevent possible contact infection or poisoning caused by harmful microorganisms such as bacterial pathogens attached to their surface.

As means of conferring antimicrobial properties, methods have been known wherein a metal thin film is attached to the surface of the article. As antimicrobial metal thin films, paper and plastic films have been proposed that have a thin film of metal such as copper, silver or alloy thereof attached to their surface.

For example, Patent Literature 1 discloses a Sn—Cu alloy film containing a Sn—Cu alloy and 1 to 10 wt % of $SnO_2$, as an antimicrobial metal thin film to be laid on a substrate. The literature discloses that the Sn—Cu alloy film is formed by forming a Sn layer and Cu layer by sputtering followed by an annealing treatment at high temperatures.

Studies been made to increase the wear resistance of metal thin films having antimicrobial properties. For example, Patent Literature 2 discloses a metal fibrous body containing fibers and metal coatings attached thereon, the surface of the coating exhibiting orange peel. The metal coating with orange peel surface is disclosed as having high adhesion strength and antimicrobial properties. In addition, Patent Literature 3 discloses an antimicrobial substrate having a base and a plurality of antimicrobial metal islands disposed on a surface of the base. The literature discloses that adjustment of contact angle of the antimicrobial metal islands can increase the wear resistance to maintain the antimicrobial properties for a long period of time.

CITATION LIST

Patent Literature

PTL 1
Japanese Patent Application Laid-Open No. 2006-342418
PTL 2
Japanese Patent Application Laid-Open No. 2001-234468
PTL 3
WO2008/047810

SUMMARY OF INVENTION

Technical Problem

However, the metal thin film of Patent Literature 1 has a drawback of unsatisfactory wear resistance.

The metal thin films of Patent Literatures 2 and 3 shows the particular surface profile and therefore their wear resistance is considered to be high to some extent. However, the wear resistance of the thin films was not satisfactory. Moreover, since these metal thin films are not made of Cu—Sn alloy, their corrosion resistance was not satisfactory.

The present invention was made under the foregoing circumstances in the art and an object thereof is to provide an antimicrobial raw material having high wear resistance as well as high antimicrobial properties and corrosion resistance; a method of producing the same, and an antimicrobial material.

Solution to Problem

The inventors have established that, in order to allow a copper-tin alloy layer to exhibit both antimicrobial properties and corrosion resistance, it is only necessary to adjust the alloy ratio between copper and tin to fall within a specific range.

The inventors have also established that, in order to increase the wear resistance of the copper-tin alloy layer, it is important to reduce the surface breakage of the copper-tin alloy layer, and that an increased wear resistance cannot be attained merely by increasing surface hardness and it is important to lessen the forces caused by friction. The inventors have also established that it is important to improve slippage of the surface of the copper-tin alloy layer. In order to achieve the foregoing, the copper-tin alloy layer preferably has such a crystal structure in which moderately sized grains are present at a moderate density and in which an amorphous phase of $Cu_3Sn$ is present among the grains. The grains present in the copper-tin alloy layer according to the present invention are granular substances which are presumably composed of a mixture of two or more different types of crystalline phase.

The presence of amorphous phase in the copper-tin alloy layer is considered to confer to the copper-tin alloy layer a moderate level of flexibility and to lessen the forces caused by friction. Moreover, the presence of moderately sized grains on the surface of the copper-tin alloy layer at a moderate density is considered to allow for improvement of slippage of the copper-tin alloy layer surface.

The crystal structure of the copper-tin alloy layer may be adjusted by the composition of the crystalline phase. A copper-tin alloy layer containing a larger amount of $Cu_{41}Sn_{11}$ phase is highly crystalline and has a high hardness. Additionally, it is often the case that few grains are present on the surface of the copper-tin alloy layer containing a larger amount of $Cu_{41}Sn_{11}$ phase. On the other hand, a copper-tin alloy layer containing a larger amount of $Cu_3Sn$ phases is less crystalline (close to amorphous) and has a low hardness. Additionally, grains are present on the surface of the copper-tin alloy layer containing a larger amount of $Cu_3Sn$ phase. Due to crystal growth, the grains may be formed in relatively large size and/or at a high density.

Specifically, in order to obtain a copper-tin alloy layer with a crystal structure in which moderately sized grains are present on the surface at a moderate density and in which amorphous phase is present among the grains, it was established that the content ratio of $Cu_{41}Sn_{11}$ phase to $Cu_3Sn$ phase in the copper-tin alloy layer is preferably adjusted. It was also established that the crystal structure and content ratio of $Cu_{41}Sn_{11}$ phase to $Cu_3Sn$ phase correlate with a Q value derived from sheet resistance. That is, it was established that a copper-tin alloy layer with a Q value that falls within a specific range exhibited the above-described crystal structure and thus has high wear resistance. The present invention was made based on such findings.

A first aspect of the present invention relates to the antimicrobial raw materials and methods of producing the same given below.

[1] An antimicrobial raw material including:
 a substrate layer; and
 a copper-tin alloy layer disposed on the substrate layer, the copper-tin alloy layer containing over 60 atomic % to 90 atomic % of copper and 10 atomic % to less than 40 atomic % of tin, wherein
  the copper-tin alloy layer comprises a $Cu_{41}Sn_{11}$ crystalline phase and a $Cu_3Sn$ crystalline phase; and
  a Q value ($\Omega/(nm \cdot Cu$ atomic %)) obtained by dividing a sheet resistance ($\Omega$) of the copper-tin alloy layer by a product of a thickness of the copper-tin alloy layer and a copper content (Cu atomic %) in the copper-tin alloy layer is $1.5 \times 10^{-4}$ to $6.0 \times 10^{-4}$.

[2] The antimicrobial raw material according to [1], wherein the substrate layer is made of resin, natural fiber or paper, the resin, natural fiber or paper having a temperature under load of 115° C. or below as measured in accordance with ASTM-D648-56 under a load of 1,820 kPa.

[3] The antimicrobial raw material according to [1] or [2], wherein a ratio of the $Cu_{41}Sn_{11}$ crystalline phase to the $Cu_3Sn$ crystalline phase in the copper-tin alloy layer, $Cu_{41}Sn_{11}/Cu_3Sn$, is 0.002 to 0.040.

[4] The antimicrobial raw material according to any one of [1] to [3], wherein a surface roughness Rz of a surface of the copper-tin alloy layer, the surface being remote from the substrate layer, is 14.4 to 15.9 nm.

[5] The antimicrobial raw material according to any one of [1] to [4], wherein the substrate layer is made of polyethylene terephthalate, polyethylene naphthalate, polypropylene, polyethylene, or polyimide.

[6] The antimicrobial raw material according to any one of [1] to [5], wherein the copper-tin alloy layer is formed by simultaneous vapor deposition using an evaporation source composed of a copper-tin alloy containing over 60 atomic % to 85 atomic % of copper and 15 atom % to less than 40 atom % of tin.

[7] The antimicrobial raw material according to any one of [1] to [6], wherein the copper-tin alloy layer covers the entire or part of an outermost surface of the antimicrobial raw material.

[8] The antimicrobial raw material according to any one of [1] to [7], wherein the substrate layer is a nonwoven fabric, woven fabric or yarn.

[9] An antimicrobial raw material including:
 a substrate layer; and
 a copper-tin alloy layer disposed on the substrate layer, the copper-tin alloy layer containing over 60 atomic % to 90 atomic % of copper and 10 atomic % to less than 40 atomic % of tin wherein,
 a deposition amount of the copper-tin alloy of the copper-tin alloy layer is 0.025 to 1.0 mg/mm$^2$; and
 the copper-tin alloy layer comprises a $Cu_{41}Sn_{11}$ crystalline phase and a $Cu_3Sn$ crystalline phase, and a ratio of the $Cu_{41}Sn_{11}$ crystalline phase to the $Cu_3Sn$ crystalline phase, $Cu_{41}Sn_{11}/Cu_3Sn$, is 0.002 to 0.040.

[10] The antimicrobial raw material according to [9], wherein the substrate layer is a nonwoven fabric, a woven fabric or a thread.

[11] A method of producing the antimicrobial raw material according to any one of [1] to [10], including:
 providing an evaporation source composed of a copper-tin alloy containing over 60 atomic % to 85 atomic % of copper and 15 atom % to less than 40 atom % of tin;
 heating a substrate disposed so as to face the evaporation source; and
 allowing a metal vapor, generated by gasifying the copper-tin alloy from the evaporation source, to contact the substrate heated to form thereon a copper-tin alloy layer.

[12] The method of producing the antimicrobial raw material according to [11], wherein the heating of the substrate brings a temperature of the substrate to 100 to 125° C.

[13] The method of producing the antimicrobial raw material according to [11] or [12], wherein the substrate is made of resin, natural fiber or paper, the resin, natural fiber or paper having a deflection temperature under load of 115° C. or below as measured in accordance with ASTM-D648-56 under a load of 1,820 kPa.

A second aspect of the present invention relates to the antimicrobial materials given below.

[14] An antimicrobial material including the antimicrobial raw material according to any one of [1] to [10].

[15] The antimicrobial material according to [14], wherein the antimicrobial material is used as a touch panel protection film.

[16] The antimicrobial material according to [14], wherein the antimicrobial material is used as medical material.

[17] The antimicrobial material according to [14], wherein the antimicrobial material is used as purification material.

Advantageous Effects of Invention

The present invention can provide an antimicrobial raw material having high wear resistance as well as high antimicrobial properties and corrosion resistance; a method of producing the same; and an antimicrobial material.

DESCRIPTION OF EMBODIMENTS

1. Antimicrobial Raw Material

An antimicrobial raw material of the present invention includes a substrate layer and a copper-tin alloy layer disposed on the substrate layer, and optionally includes additional layer(s) as needed.

There are no particular limitations on the material of the substrate layer; the substrate layer may be made of metal, glass, ceramics, resin (including synthetic fiber), natural fiber, paper, wood, or the like. In particular, because a copper-tin alloy layer can be formed without having to perform high-temperature annealing treatment as will be described later, the substrate layer may advantageously be made of resin, natural fiber, paper, or the like.

There are no particular limitations on the resin used to constitute the substrate layer; the substrate layer may be thermoplastic or thermosetting resin. The resin preferably has a deflection temperature under load of 115° C. or below, more preferably 90° C. or below, as measured in accordance with ASTM-D648-56 under a load of 1,820 kPa. This is because resin with a deflection temperature under load of 115° C. or below offers good processability, and the resultant films also have good flexibility.

Deflection temperature under load is measured by a method that complies with ASTM-D648-56. Specifically, deflection temperature under load can be measured as the temperature at which the bending strain of a test specimen, loaded on an apparatus for flatwise test and heated at a constant heating rate of 2 C.°/min, reaches 0.2% under a load of 1,820 kPa. The test specimen is 80 mm in length, 10 mm in width and 4 mm in thickness, and distance between grips may be set to 64 mm.

Examples of resins having a deflection temperature under load of 115 C.° or below include polyester resins, polyolefin resins, and polyamide resins, with polyester resins and polyolefin resins being preferable. Examples of the polyester resins include polyethylene terephthalate and polyethylene naphthalate. The polyolefin resins may be homopolymers of α-olefins or copolymers of α-olefins and different comonomers. The α-olefin in the polyolefin resins may be, for example, ethylene or propylene. Examples of such polyolefin resins include polyethylene and polypropylene. Examples of the polyamide resins include nylon 6 and nylon 66.

The substrate layer may be a film, nonwoven fabric or woven fabric. In cases where the woven fabric is used as the substrate layer, formation of a copper-tin alloy layer described later improves tension strength of the woven fabric and provides some advantages of improving strength of the whole fabric, e.g., less susceptible to tearing and/or deformation. The textile weave of the woven fabric is not particularly restricted and can be, for example, plain weave or the like.

The thickness of the substrate layer may be, for example, about 5 μm to about 700 μm, although it depends on the intended application of the antimicrobial raw material. When the substrate layer is excessively thin, the mechanical strength of the antimicrobial raw material decreases.

In order to increase the interface adhesion strength of the substrate layer to a copper-tin alloy layer which will be described later, the substrate layer may be subjected to chemical or physical surface treatment on the surface. Any of the surface treatments known in the art can be employed and there are no particular limitations; specific examples thereof include plasma treatment under reduced pressure, plasma treatment under atmospheric pressure, corona treatment, vapor deposition, and CVD.

A copper-tin alloy layer has a function of imparting an antimicrobial activity to the substrate layer. Accordingly, the copper-tin alloy layer is preferably disposed on the outermost surface of the antimicrobial raw material.

The copper-tin alloy layer preferably contains over 60 atom % to 90 atom % of copper and 10 atom % to less than 40 atom % of tin; more preferably contains 63 atom % to 90 atom % of copper and 10 atom % to 37 atom % of tin; still more preferably contains 15 atom % to less than 37 atom % of tin, with the remaining being substantially copper; and particularly preferably contains 20 atom % to 30 atom % of tin, with the remaining being substantially copper. A tin content in the copper-tin alloy of less than 10 atom % may result in changes in appearance due to corrosion or color change by contact with water, salted water, body fluid and/or the like. Further, antimicrobial activity increases with increasing copper content.

The copper-tin alloy layer may contain additional element(s) as long as the above-described copper content and tin content are satisfied. By the addition of such element(s), economic efficiency, affinity for liquids, affinity for substrates, color tone of the metal thin film and/or the like may be adjusted. For example, the copper-tin alloy may contain such metals as aluminum, germanium, berylium, nickel and/or silicon, which have vapor pressures close to that of copper in melted state. The copper-tin alloy layer may also contain additional antimicrobial metals such as zinc, silver and/or nickel, as long as corrosion resistance is not compromised.

Alloying of copper with tin for improved corrosion resistance has been widely conducted in the field of bulk metal materials. However, even today, the upper limit of the tin content in copper-tin alloy, which has been used as bronze since ancient times, is about 10 atom %. Copper-tin alloys that contain greater than 10 atom % of tin become more brittle. Thus, although such copper-tin alloys may be used as a cast metal, they are not usually used as plate or rod material that is subsequently subjected to plastic working process.

Since the copper alloy in the antimicrobial raw material of the present invention is provided in the form of thin film disposed on the substrate layer, even when a copper-tin alloy containing greater than 10 atom % of tin is used, the antimicrobial raw material has processability and durability during use.

As described above, in order to enhance the wear resistance of the copper-tin alloy layer, it is important to be able to lessen the forces caused by friction, and to improve the slippage of the surface of the copper-tin alloy layer. In order to achieve the foregoing, it is presumed that a copper-tin alloy layer is preferable that has a crystal structure in which moderately sized grains are present on the surface at a moderate density and in which amorphous phase is present among the grains. The amorphous phase as used in the present invention encompasses not only a complete amorphous phase with no crystallinity, but also an amorphous phase having a little crystallinity.

The copper-tin alloy layer having such a crystal structure can be obtained by adjusting the composition of the crystalline phase. That is, the copper-tin alloy layer includes $Cu_{41}Sn_{11}$ phase and $Cu_3Sn$ phase, and optionally includes $Cu_{5.6}Sn$ phase as necessary.

A copper-tin alloy layer containing a large amount of $Cu_{41}Sn_{11}$ phase is highly crystalline and has high hardness. Additionally, few grains are present on the surface of the copper-tin alloy layer containing a large amount of $Cu_{41}Sn_{11}$ phase. On the other hand, a copper-tin alloy layer containing a large amount of $Cu_3Sn$ phase is less crystalline (i.e., includes a large amount of amorphous phase) and has low hardness. Additionally, grains are present on the surface of the copper-tin alloy layer containing a large amount of $Cu_3Sn$ phase. Due to crystal growth, the grains may be formed in relatively larger size and/or at a high density.

Specifically, in order to obtain a copper-tin alloy layer having the above-described crystal structure, it is preferred to adjust the content ratio between $Cu_{41}Sn_{11}$ phase and $Cu_3Sn$ phase in the copper-tin alloy layer to fall within a appropriate range. The content ratio of $Cu_{41}Sn_{11}$ phase to $Cu_3Sn$ phase in the copper-tin alloy layer, $Cu_{41}Sn_{11}/Cu_3Sn$, is preferably 0.002 to 0.040, and more preferably 0.002 to 0.010. As described above, when the content ratio $Cu_{41}Sn_{11}/Cu_3Sn$ is too small, the $Cu_3Sn$ phase content is so high that it results not only in excessively low hardness but also in grains being grown too large or formed at an excessively high density. On the other hand, when the $Cu_{41}Sn_{11}/Cu_3Sn$ ratio is too high, the $Cu_{41}Sn_{11}$ content is so high that it results not only in excessively high hardness but also in formation of few grains. As will be described later, the content ratio $Cu_{41}Sn_{11}/Cu_3Sn$ can be adjusted by the heating temperature of the substrate upon vapor deposition of the copper-tin alloy layer.

The content ratio $Cu_{41}Sn_{11}/Cu_3Sn$ can be determined based on the ratio of intensity of peaks ascribed to $Cu_{41}Sn_{11}$ and to $Cu_3Sn$, respectively. The peak intensities are obtained by XRD measurement of the copper-tin alloy layer. The peak ascribed to $Cu_{41}Sn_{11}$ is a peak at a $2\theta(°)$ of around 42.74, and the peak ascribed to $Cu_3Sn$ is a peak at a $2\theta(°)$ of around 43.26 (where $\theta$ is an angle of incidence of an X-ray to the surface of the copper-tin alloy layer).

A Q value ($\Omega/(nm\cdot Cu$ atomic percent)) derived from sheet resistance ($\Omega$) of the copper-tin alloy layer correlates with the crystal structure and the content ratio of $Cu_{41}Sn_{11}$ phase to $Cu_3Sn$ phase. That is, a Q value of a copper-tin alloy layer is higher when the copper-tin alloy layer has a crystal structure containing more $Cu_{41}Sn_{11}$ phase without grains; whereas a Q value is lower when the copper-tin alloy layer has a crystal structure containing more $Cu_3Sn$ phase with grains. Thus, whether the copper-tin alloy layer has the above-described crystal structure copper-tin alloy layer can be determined based on the Q value. Therefore, in order to increase the wear resistance, the Q value of the copper-tin alloy layer is preferably $1.5 \times 10^{-4}$ to $6.0 \times 10^{-4}$, and more preferably $1.5 \times 10^{-4}$ to $5.0 \times 10^{-4}$.

The Q value ($\Omega/(nm\cdot Cu$ atom %)) of the copper-tin alloy layer can be measured by the following procedure.

1) Measure sheet resistance ($\Omega$) of a surface of the copper-tin alloy layer by the direct current four terminal method.

2) Calculate a Q value ($\Omega/(nm\cdot Cu$ atomic %)) by dividing the obtained value of sheet resistance ($\Omega$) by a product of thickness (nm) of the copper-tin alloy layer and copper atom content in the layer (Cu atomic %).

Surface roughness Rz of a surface of copper-tin alloy layer, the surface being remote from the substrate layer, i.e., the surface where the copper-tin alloy layer being exposed, is preferably 14.4 to 15.9 nm, and more preferably 15.0 to 15.9 nm. Because a copper-tin alloy layer with a higher $Cu_3Sn$ phase content has grains, surface roughness Rz tends to be larger. On the other hand, because a copper-tin alloy layer with a higher $Cu_{41}Sn_{11}$ phase content has few grains, surface roughness Rz tends to be smaller. Specifically, since copper-tin alloy layers with surface roughness Rz being in the above-described range have moderately sized grains at a moderate density, it is considered that surface slippage can be further increased.

Surface roughness Rz of the surface of the copper-tin alloy layer can be measured with a scanning probe microscope (SPM).

There are no particular limitations on the thickness of the copper-tin alloy layer as long as the layer is thick enough to allow required antimicrobial properties to be maintained, and is preferably 200 nm or less, and more preferably 100 nm or less. When making the copper-tin alloy layer translucent, the thickness is preferably 50 nm or less, more preferably 30 nm or less. The thickness of the copper-tin alloy layer is preferably 5 nm or more, more preferably 10 nm or more. This is to entirely cover the surface of the substrate layer with the copper-tin alloy layer as well as to obtain uniform antimicrobial activity.

When the substrate layer is provided as woven fabric, non-woven fabric or the like, the deposition amount of the copper-tin alloy is preferably 1.0 m g/mm² or less, more preferably 0.5 mg/mm² or less. When making the copper-tin alloy layer translucent, the deposition amount of copper-tin alloy is preferably 0.25 mg/mm² or less, more preferably 0.15 mg/mm² or less. The deposition amount of copper-tin alloy is preferably 0.025 mg/mm² or more, more preferably 0.05 mg/mm² or more. This is to entirely cover the surface of the substrate layer with the copper-tin alloy layer as much as possible as well as to obtain uniform antimicrobial activity.

The antimicrobial raw material of the present invention may further include an adhesive layer on a surface of the substrate layer, which surface is remote from the copper-tin alloy layer. The adhesive layer is preferably such that it allows the antimicrobial raw material once applied to the article surface to be detached (releasable adhesive layer). The reason for this is that the antimicrobial raw material needs to be detached in such cases where antimicrobial activity and other properties have deteriorated due to attachment of dust on the surface of the copper-tin alloy layer, or where appearance has been impaired.

There are no particular limitations on the type of the adhesive agent used for the adhesive layer; any of rubber adhesive agents, acrylic adhesive agents, silicone adhesive agents, urethane adhesive agents and other adhesive agents may be used.

The antimicrobial raw material of the present invention may include additional layer(s) as needed. The additional layer may be a layer having water absorbability, water repellency, light scattering property, surface smoothness, good appearance (e.g., color or gloss) or other property. From the perspective of producing inexpensive antimicrobial raw materials, the copper-tin alloy layer is preferably formed directly on the substrate layer.

2. Method of Producing Antimicrobial Raw Material

The antimicrobial raw material of the present invention is produced by forming the copper-tin alloy layer by vacuum vapor deposition on at least one side of the substrate layer. This is because, unlike the formation of the copper-tin alloy layer by sputtering or electroplating, vacuum vapor deposition eliminates the need of high-temperature annealing of a laminate of copper and tin layers for alloying.

On the other hand, when an alloy thin film is to be formed by vacuum vapor deposition, an adjustment is required such that the ratio of evaporation rate of the alloy elements is kept constant. This is because the vapor pressure of a metal at a particular temperature significantly varies from one element to another, so too does the evaporation rate.

Specifically, when an alloy evaporation source is heated and melted, only an element with higher vapor pressure (element A) first evaporates, and after element A has almost evaporated leaving little amount of element A in the evaporation source, the evaporation rate of an element with lower vapor pressure (element B) gradually increases and eventually only element B evaporates. Alloys with a controlled composition range cannot be obtained in such a process. For this reason, commonly, two or more separate evaporation sources are prepared, each of which contains one of the alloy elements. The heating temperature of each evaporation source is then independently controlled so as to control the ratio of evaporation rate of the alloy elements. As a matter of course, such a control scheme causes an increase in film formation costs.

Figure 1:
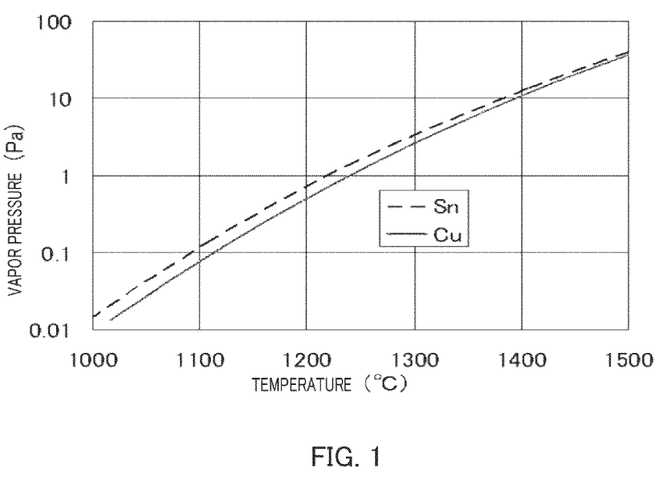
FIG. 1 is a graph showing temperature dependency of the vapor pressures of copper and tin.

As shown in FIG. 1, copper and tin have very similar vapor pressure over a wide temperature range from 1,050 C.° to 1,500 C.°. Thus, it has been established that even when a single copper-tin alloy evaporation source is used, it is possible to produce a copper-tin alloy deposited film with a relatively controlled alloy composition, in contrast to cases where alloy systems other than copper-tin alloy are used.

It should be noted, however, that the composition of the evaporation source does not necessary match the composition of the resultant deposited film; the composition of the deposition film is determined by various factors including specific gravity in melted state, in addition to vapor pressure of respective alloy metals. For this reason, it is difficult to predict the metal composition of the deposited thin film.

As a result of extensive studies, the inventors have also established that in copper-tin alloy systems, when the tin proportion is 15 atom % to less than 40 atom %, preferably 24 atom % to 33 atom %, the composition of the evaporation source becomes close to that of the deposited film. It is generally known that when deposition is continuously conducted using an alloy evaporation source, some of the alloy elements predominantly evaporate and thereby the composition of the remaining evaporation source deviates from the original composition, so that the composition of the film being deposited likewise gradually deviates from the original composition. The inventors have also established that the amount of deviation in composition can be relatively reduced when the tin proportion in the deposited film is 15 atom % to less than 40 atom %, preferably 24 atom % to 33 atom %. It is thus possible to efficiently form thin films of antimicrobial metal without having to perform any special additional step, such as addition of any of the constituent metals during the deposition process.

A copper-tin alloy deposited film produced from a single alloy evaporation source are not only cost-effective compared to those produced using two or more evaporation sources, but tend to have a uniform alloy composition. Thus, in the present invention, it is preferable to form the copper-tin alloy layer by simultaneous vapor deposition using a single alloy evaporation source.

In the present invention, in order to form a copper-tin alloy layer having the crystal structure described above, it is important to heat the substrate to a predetermined temperature upon of vacuum vapor deposition of the copper-tin alloy layer.

That is, the antimicrobial raw material of the present invention is produced by the steps of: providing an evaporation source consisting of copper-tin alloy; 2) heating a substrate placed so as to face the evaporation source; and allowing a metal vapor, generated by gasifying the copper-tin alloy from the evaporation source, to contact the heated substrate to form thereon a copper-tin alloy layer.

The evaporation source in step 1) is preferably an evaporation source composed of a copper-tin alloy which contains over 60 atom % to 85 atom % of copper and 15 atom % to less than 40 atom % of tin. This is because an evaporation source having the foregoing composition results in a copper-tin alloy layer whose composition is less deviated from the composition of the evaporation source.

In steps 2) and 3), the substrate is heated to a predetermined temperature in order to obtain a copper-tin alloy layer having the crystal structure described above. That is, by heating the substrate, a copper-tin alloy layer that also contains $Cu_3Sn$ phase (in addition to $Cu_{41}Sn_{11}$ phase) is obtained. It is preferred that the heating of the substrate be continuously carried out during vapor deposition of the copper-tin alloy layer.

Heating temperature varies depending on the type of substrates and is preferably 100 to 125° C., and more preferably 110 to 120° C. When the temperature of the substrate is too high, the above-described crystal structure is not formed due to too high $Cu_3Sn$ phase content, resulting in an excessively low Q value. When the temperature of the substrate is too low, the above-described crystal structure is not formed due to too high $Cu_{41}Sn_{11}$ phase content, resulting in an excessively high Q value. For instance, when the temperature of the substrate is 90° C. or below, almost all of the crystalline phases are $Cu_{41}Sn_{11}$ phase, and when the temperature is 130° C. or above, almost all of the crystalline phases are $Cu_3Sn$ phase.

Heating of the substrate may be accomplished by any manner; heating may be carried out for example using a sheet heater or the like.

When the antimicrobial raw material of the present invention is a nonwoven fabric or woven fabric, it can be produced by forming a thin film on a resin film or paper; and then cutting the obtained film or paper with the thin film, followed by mixing with other components or materials.

As seen above, in the present invention, a vapor-deposited alloy film can be obtained by simultaneous vapor deposition from a single alloy evaporation source, wherein the composition of the vapor-deposited alloy film is less deviated from the composition of the evaporation source.

This eliminates the need for conventional lamination of a Cu layer and a Sn layer and subsequent high-temperature annealing for alloying of Cu and Sn. Thus, the copper-tin alloy layer can also be formed on low-heat resistant substrate layers such as those described above.

3. Application of Antimicrobial Raw Material

The antimicrobial raw material of the present invention, as described earlier, has high antimicrobial properties and corrosion resistance. Thus, the antimicrobial raw material of the present invention is suitably used as various types of antimicrobial raw materials. Examples of the antimicrobial raw materials include medical materials, materials for household, purification materials, materials for agriculture, various types of surface protection films and the like.

Examples of the medical materials include medical equipment, drug containers, personal protectors for infection prevention (including masks), bandages, dressing films for wounds, adhesive bandages and the like. Examples of the materials for household include storage vessels or materials for packing for food products, drinking water, daily life water, flowers and ornamental plants, or the like; materials for kitchen such as cutting boards, materials for food garbage disposal or the like; materials for bathroom such as washbowls, chairs or the like; materials for bed bath; facecloth, dishcloth, dust cloth or the like; materials for outfitting such as clothes, footwear, bags (in particular backing fabrics of sports bags, pouches, business bags, and suitcases) or the like; materials for house such as curtain, carpet, bedclothes, beddings or the like; and materials for hygiene such as masks, portable toilets, sheets for toilet seat, paper diapers, sanitary protection products or the like. Examples of the purification materials include gas purification filters, liquid purification filters and the like. Examples of the materials for agriculture include multi sheets, filters for water culture, sheets for plant nursery box, bags for hanging fruits, light reflecting sheets for fruit coloring and the like. Examples of the surface protection films include protective films for touch panel that can be put on a touch panel screen of a display unit, and the like.

The antimicrobial raw material of the present invention can be processed into an appropriate shape as necessary and used as materials for buildings that are put on the surface of various building structures. Examples of such materials for buildings include materials for buildings that are put on lavatories, rest rooms, bath rooms, shower rooms, laundry rooms, ducts for air circulation, drain pans of air conditioner and hot water supply rooms in various facilities; kitchens in commercial facilities handling food products; boundary areas between general wards and isolation wards, areas before entering an intensive care unit, and medical device in medical facilities; rooms before entering clean room in semiconductor manufacturing facilities; building structures such as entrances, footwear dropping rooms or the like in various building structures; wall surfaces, floor surfaces, surfaces of fittings in building structures; or surfaces of doors, windows, handrails, electric switches, kitchen counters, sinks, faucets, bathtubs, toilet bowls, furniture or store fixtures that are placed in those building structures; and the like.

EXAMPLES

The present invention will now be further described below with reference to Examples and Comparative Examples, which however shall not be construed as limiting the scope of the present invention.

Example 1

As a substrate film, a polyethylene terephthalate film with a thickness of 25 μm (deflection temperature under load (at a load of 1820 kPa): 104° C.) was provided. This substrate film was set 400 mm above an evaporation source in a vapor deposition apparatus. A sheet heater was then placed at the back side of the substrate film (i.e., side remote from a vapor-deposited alloy film to be deposited) and heated such that the temperature of the substrate film was at 120° C.

In addition, 60 g of pure copper granules (99.9% purity) of 1 to 2 mm size and 40 g of pure tin granules (99.9% purity) of 1 to 2 mm size were weighed (100 g in total). The granules were placed in a metal vessel and mixed well to provide an evaporation source containing 77 atomic % of copper and 23 atomic % of tin (equivalent to 60 wt % of copper and 40 wt % of tin). The evaporation source was placed in a melting pot in the vapor deposition apparatus and subjected to vacuum evacuation until the pressure reached $10^{-3}$ Pa or less. Next, the melting pot and evaporation source were slowly heated using electron beams such that the evaporation source did not scatter to a large degree, allowing the evaporation source in the melting pot to be completely molten to afford an alloy evaporation source.

The alloy evaporation source was once allowed to cool in vacuum and heated again by exposure with electron beams, whereby a copper-tin alloy layer was deposited on the substrate film placed about 400 mm above the evaporation source. The film deposition rate was set to 10 to 15 nm per second.

Example 2

A copper-tin alloy layer was formed on a substrate film in the same manner as in Example 1 except that the temperature of the substrate film at the time of vapor deposition was changed as shown in Table 1.

Comparative Examples 1 to 4

Copper-tin alloy layers were formed on substrate films in the same manner as in Example 1 except that the temperature of the substrate film at the time of vapor deposition was changed as shown in Table 1.

(Evaluation)

For copper-tin alloy layers obtained in Examples 1 and 2 and Comparative Examples 1 to 4, 1) analysis of alloy composition, 2) measurement of surface roughness Rz, 3) measurement of sheet resistance and Q value, 4) wear resistance test, 5) XRD analysis, 6) SEM observation, 7) antimicrobial performance test and 8) durability test were carried out in the manner described below.

1) Analysis of Alloy Composition

A part of the obtained film was cut into a square piece of about 3 mm on each side to prepare a sample film. Metal atoms contained in the copper-tin alloy layer of the sample film were detected by energy dispersive X-ray spectroscopy (EDS). Among the detected metal atoms, the atomic percentage of additive element (tin) was determined, excluding copper. In this way, the alloy composition of the obtained copper-tin alloy layer was determined.

2) Measurement of Surface Roughness Rz Surface roughness Rz of the copper-tin alloy layer of the obtained film was measured with a scanning probe microscope (SPM, manufactured by SII NanoTechnology, SPI-3800N) under the following conditions.

Measurement mode: DFM
Cantilever: SI-DF20
Measurement range: 1 μm×1 μm

3) Measurement of Sheet Resistance and Q Value

The obtained film was cut into a piece of predetermined size to prepare a sample film. Electrodes of four termini composed of current source termini of a current supply equipment and voltage sensing termini of voltage measurement equipment were pressed against the surface of the copper-tin alloy layer of the sample film. Sheet resistance (Ω) was measured from voltage change when the following direct current electricity was applied to the surface of the copper-tin alloy layer of the sample film by the direct current four terminal method.

Direct current electricity: $1 \times 10^{-6}$ (A), $2 \times 10^{-6}$ (A), $5 \times 10^{-6}$ (A), $1 \times 10^{-5}$ (A), $2 \times 10^{-5}$ (A), $5 \times 10^{-5}$ (A)

KEITHLEY220 PROGRAMMABLE CURRENT SOURCE was used for the current supply equipment; and KETHLEY196 SYSTEM DMM was used as a voltage application device.

A value obtained by dividing the obtained sheet resistance (Ω) by a product of the thickness of the copper-tin alloy layer (nm) and the atomic percentage of copper contained in the copper-tin alloy layer was designated as "Q value (Ω/(nm·Cu atomic %))."

4) Wear Resistance Test

A surface of the copper-tin alloy layer of the sample film was rubbed with a felt cloth wetted with water under a condition of 3 kgf load. The number of rubbing cycles it takes to visually change the color of the substrate layer was counted.

A: The number of rubbing cycles was not less than 500.
B: The number of rubbing cycles was less than 500.

5) XRD Analysis

The obtained film was cut into a piece of predetermined size to prepare a sample film. The XRD of the copper-tin alloy layer of the sample film was measured with analyzer RINT-1500 (manufactured by Rigaku) under the following conditions.

X-ray target: Cu
X-ray: Cu K ALPHA1
Goniometer: Wide angle goniometer
Scanning speed: 2°/min
Scanning step: 0.02°
Scanning range: 3 to 100°

With an angle of incidence of an X-ray to the surface of the copper-tin alloy layer being defined as θ, the intensity of a peak ascribed to $Cu_{41}Sn_{11}$ at a 2θ(°) of around 42.74 and the intensity of a peak ascribed to $Cu_3Sn$ at a 2θ(°) of around 43.26 were measured to calculate the ratio of peak intensity of $Cu_{41}Sn_{11}$ and $Cu_3Sn$, $Cu_{41}Sn_{11}/Cu_3Sn$.

Figure 2A:
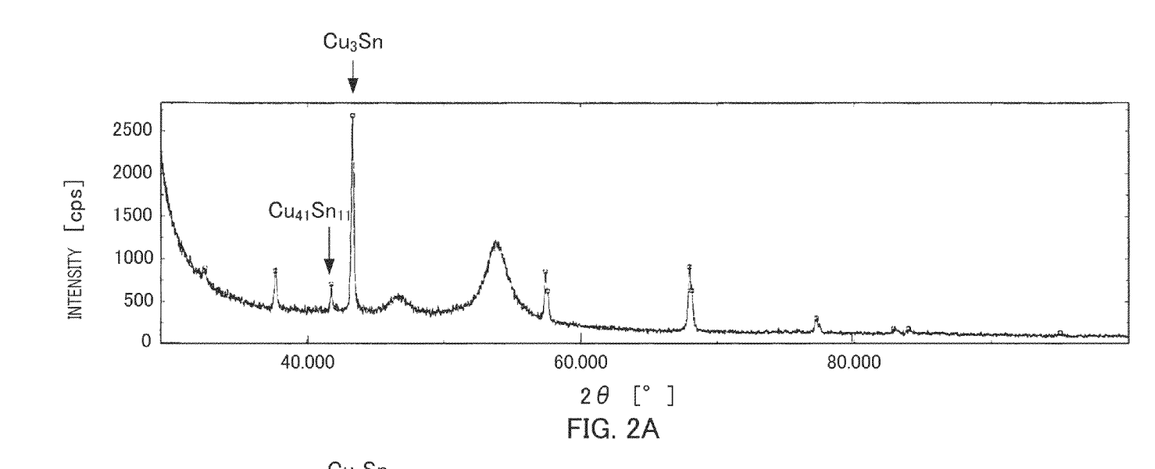
FIG. 2 shows the results of XRD analysis in Example 1.
Figure 2B:
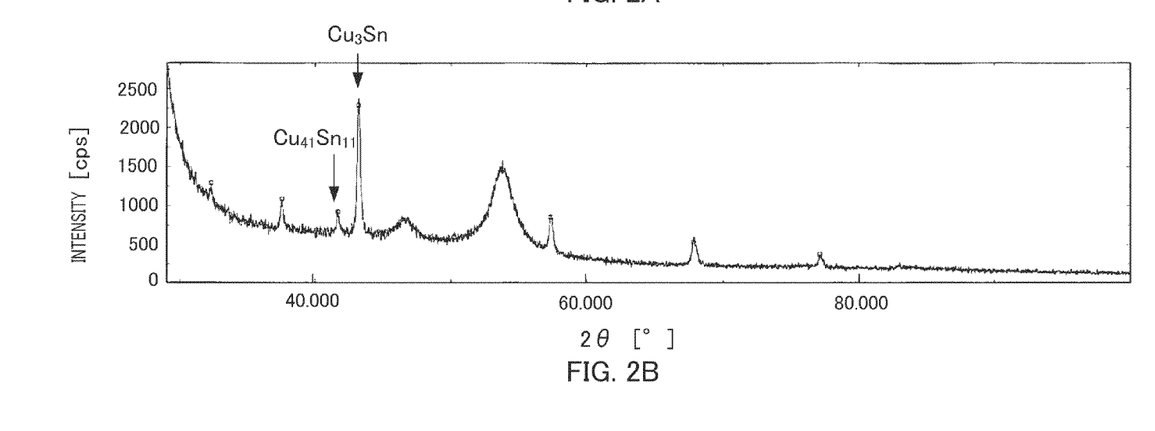

FIG. 2A shows the results of the XRD analysis of the copper-tin alloy layer in Example 1 before wear resistance test; and FIG. 2B shows the results of the XRD analysis of the copper-tin alloy layer after wear resistance test. FIG. 3A shows the results of the XRD analysis of the copper-tin alloy layer in Example 2 before wear resistance test; and FIG. 3B shows the results of the XRD analysis of the copper-tin alloy layer after wear resistance test. FIG. 4A shows the results of the XRD analysis of the copper-tin alloy layer in Comparative Example 1 before wear resistance test; and FIG. 4B shows the results of the XRD analysis of the copper-tin alloy layer after wear resistance test. In the drawings, the horizontal axis represents $2\theta(°)$ where $\theta$ is an angle of incidence, and the vertical axis represents an peak intensity (cps).

6) SEM Observation

Figure 5A:
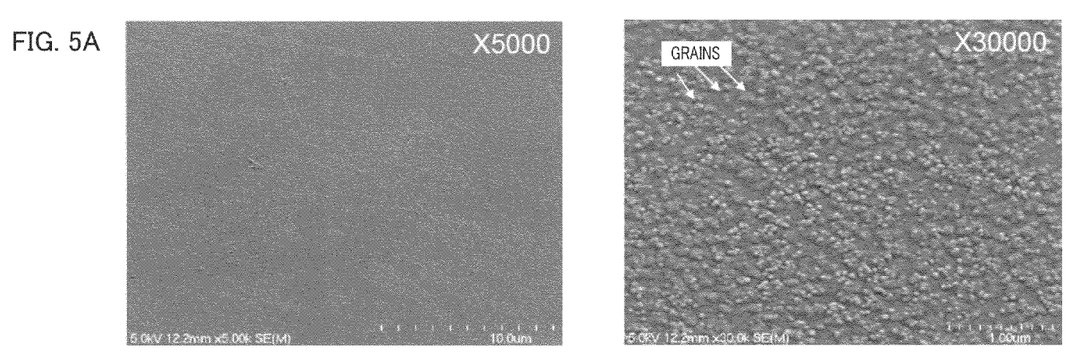
FIG. 5 shows an SEM image of a surface of a copper-tin alloy layer in Example 1.
Figure 5B:
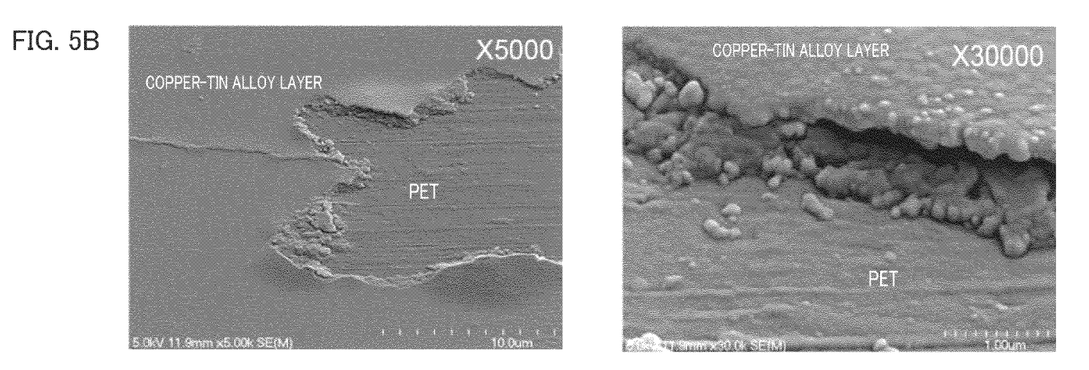
Figure 6A:
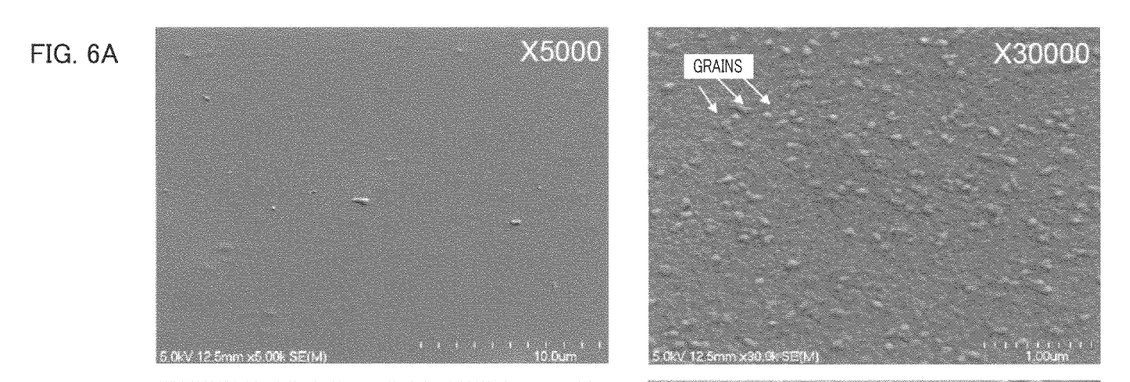
FIG. 6 shows an SEM image of the surface of a copper-tin alloy layer in Example 2.
Figure 6B:
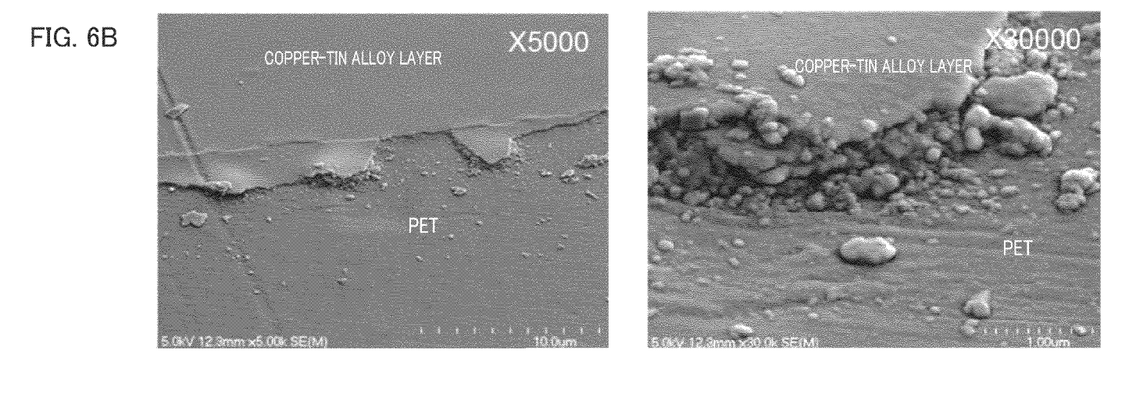
Figure 7A:
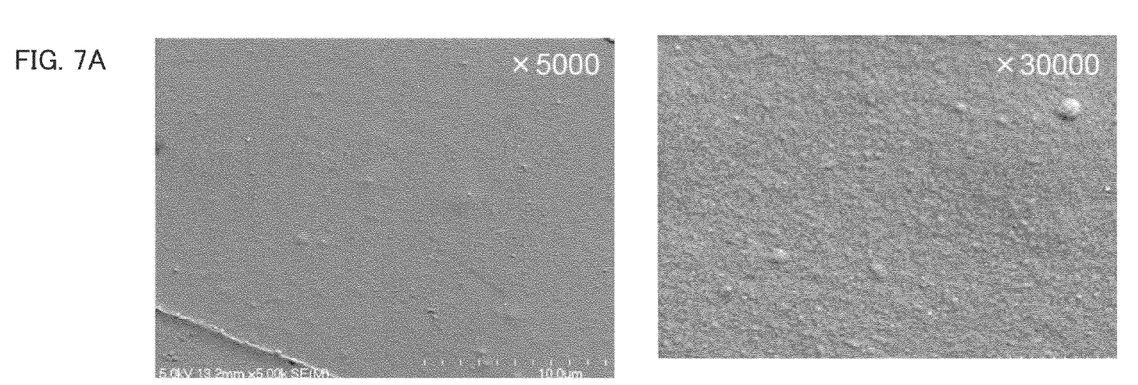
FIG. 7 shows an SEM image of the surface of a copper-tin alloy layer in Comparative Example 1.
Figure 7B:
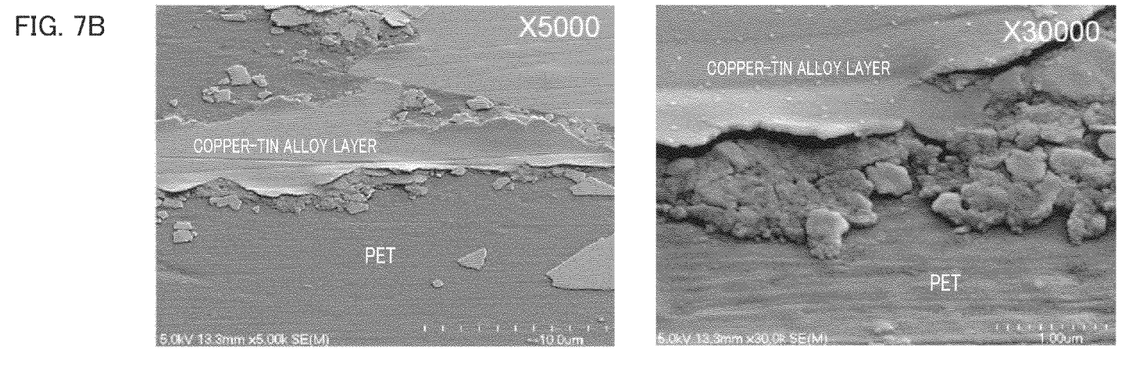

A surface of the copper-tin alloy layer of the obtained film was measured by a scanning electron microscope (manufactured by Hitachi Ltd. S-4700N) under conditions at a magnification of 5000× and 30000×. FIG. 5A shows an SEM image of the surface of the copper-tin alloy layer in Example 1 before wear resistance test; FIG. 5B shows an SEM image of the surface of the copper-tin alloy layer after wear resistance test. FIG. 6A shows an SEM image of the surface of the copper-tin alloy layer in Example 2 before wear resistance test; FIG. 6B shows an SEM image of the surface of the copper-tin alloy layer after wear resistance test. FIG. 7A shows an SEM image of the surface of the copper-tin alloy layer in Comparative Example 1 before wear resistance test; FIG. 7B shows am SEM image of the surface of the copper-tin alloy layer after wear resistance test.

7) Antimicrobial Performance Test

The obtained film was cut into a square of about 50 mm on each side to prepare a sample film. An antimicrobial test in accordance with JIS Z 2801 was carried out for the sample film using *Staphylococcus aureus*.

The numbers of bacterial colonies detected after test are listed in Table 1 as bacteria counts (A) after 24 hours. When no bacteria were detected, "<10" is designated in Table 1. At the same time, the number of bacterial colonies on a polyethylene plate (control) was detected and divided by bacteria count (A), and the common logarithm of the resulting value was calculated to find an antimicrobial activity. Values of antimicrobial activity are listed in Table 1. The test was carried out more than once, and an average of the numbers of the bacterial colonies was calculated.

8) Durability Test 8-1) Durability Test (Deterioration by Contact with Hot Water)

The obtained film was cut into a square of about 50 mm on each side to prepare a sample film, and the sample film was attached to the wall of a bath room. A flow of water at 40±2° C. was applied to the surface of the sample film using a hand shower for 30 seconds and then water droplets of the same temperature were scattered to the surface of the film, after which the adhered water droplets were allowed to dry naturally without being wiped off. This series of operations was carried twice a day for three days and then the degree of deterioration of the metal thin film was visually evaluated. Subsequently, the same operations were carried out for another four days and the degree of deterioration of the metal thin film after the operations were carried out for a total of seven days was visually evaluated.

The degree of deterioration of the metal thin film was carried out by observing the presence of tarnishing and bare spot (peel-off) of the metal thin film.

(Tarnishing)

A: No tarnishing of the metal thin film was observed.

B: Tarnishing of the metal thin film was observed.

(Bare Spot)

The bare spot was judged by whether or not the metal thin film was peeled off (i.e., whether or not the substrate layer was exposed to be seen) after a double-sided tape was attached to and then removed from the metal thin film.

A: No bare spots (no peel-offs) of the metal thin film were observed.

B: The bare spot of the metal thin film was observed.

8-2) Durability Test (Deterioration by Contact with Salted Water)

The obtained film was cut into a square of about 50 mm on each side to prepare a sample film. The surface of this sample film was wiped while applied with pressing force at a load of 2±0.5N three times using a piece of gauze that had been dipped in physiological saline and then softly squeezed off, after which the adhered water droplets were allowed to dry naturally without being wiped off. This operation was carried twice a day for three days and then the degree of deterioration of the metal thin film was visually evaluated. Subsequently, the same operations were carried out for another four days and the degree of deterioration of the metal thin film after the operations were carried out for a total of seven days was visually evaluated.

The degree of deterioration of the metal thin film was carried out by observing the presence of tarnishing and bare spot (peel-off) of the metal thin film.

(Tarnishing)

A: No tarnishing of the metal thin film was observed.

B: Tarnishing of the metal thin film was observed.

(Bare Spot)

The bare spot was judged by whether or not the metal thin film was peeled off (to be concrete, whether or not the substrate layer was exposed to be seen) after a double-sided tape was attached to and then removed from the metal thin film.

A: No bare spots (no peel-offs) of the metal thin film were observed.

B: The bare spot of the metal thin film was observed.

The evaluation results in Examples 1 and 2 and Comparative Examples 1 to 4 are shown in Table 1.

TABLE 1

| | | | Example 1 | Example 2 | Comparative Example 1 | Comparative Example 2 | Comparative Example 3 | Comparative Example 4 |
|---|---|---|---|---|---|---|---|---|
| Film composition | Metal layer | Cu atomic %/Sn atomic % | 74/26 | 74/26 | 74/26 | 74/26 | 74/26 | 74/26 |
| | | Thickness (nm) | 50 | 50 | 50 | 50 | 50 | 50 |
| | | Crystalline phase contained | $Cu_{41}Sn_{11}$ $Cu_3Sn$ | $Cu_{41}Sn_{11}$ $Cu_3Sn$ | $Cu_{41}Sn_{11}$ | $Cu_{41}Sn_{11}$ | $Cu_3Sn$ | $Cu_3Sn$ |
| | | $Cu_{41}Sn_{11}/Cu_3Sn$ ratio | 0.002 | 0.04 | ∞ | ∞ | 0 | 0 |
| | Substrate layer | Material | PET | PET | PET | PET | PET | PET |
| | | Deflection temperature under load (° C.) | 104 | 104 | 104 | 104 | 104 | 104 |
| | | Thickness (μm) | 25 | 25 | 25 | 25 | 25 | 25 |

TABLE 1-continued

|  |  | Example 1 | Example 2 | Comparative Example 1 | Comparative Example 2 | Comparative Example 3 | Comparative Example 4 |
|---|---|---|---|---|---|---|---|
| Method of vapor deposition/ alloying | Evaporation source (Cu atomic %/Sn atomic %) | 77/23 | 77/23 | 77/23 | 77/23 | 77/23 | 77/23 |
|  | Temperature of substrate upon vapor deposition (° C.) | 120 | 110 | 23 | 90 | 130 | 140 |
|  | Annealing | None | None | None | None | None | None |
| Evaluations | Surface roughness Rz | 15.88 | 15.5 | 10.11 | 14.36 | 15.94 | 21.6 |
|  | Sheet resistance/thickness ($\Omega$/nm) | 0.013 | 0.014 | 0.056 | 0.052 | 0.01 | 0.01 |
|  | Q value $\Omega$/(nm · Cu atomic %) | 0.00018 | 0.00019 | 0.00076 | 0.0007 | 0.00014 | 0.00014 |
|  | Wear resistance test | A | A | B | B | B | B |
| Antibacterial performance test | Bacteria count after 24 hours (cfu/25 cm$^2$) | <10 | <10 | <10 | <10 | <10 | <10 |
|  | Antimicrobial activity | >4 | >4 | >4 | >4 | >4 | >4 |
| Durability test (Hot water) | Day 3 Tarnishing | A | A | A | A | A | A |
|  | Bare spot | A | A | A | A | A | A |
|  | Day 7 Tarnishing | A | A | A | A | A | A |
|  | Bare spot | A | A | A | A | A | A |
| Durability test (Contact with salted water) | Day 3 Tarnishing | A | A | A | A | A | A |
|  | Bare spot | A | A | A | A | A | A |
|  | Day 7 Tarnishing | A | A | A | A | A | A |
|  | Bare spot | A | A | A | A | A | A |

As shown in Table 1, the copper-tin alloy layers in Examples 1 and 2 in which the substrate was heated to a predetermined temperature at the time of vapor deposition were found to exhibit high antimicrobial properties and corrosion resistance as well as high wear resistance. On the other hand, it was found that the copper-tin alloy layer in Comparative Example 1 where the substrate was not heated at the time of vapor deposition, the copper-tin alloy layer in Comparative Example 2 where the heating temperature of the substrate was too low, and the copper-tin alloy layer in Comparative Examples 3 and 4 where the heating temperature of the substrate was too high all exhibited antimicrobial properties and corrosion resistance comparable to those in Examples, but exhibited low wear resistance.

Figure 3:
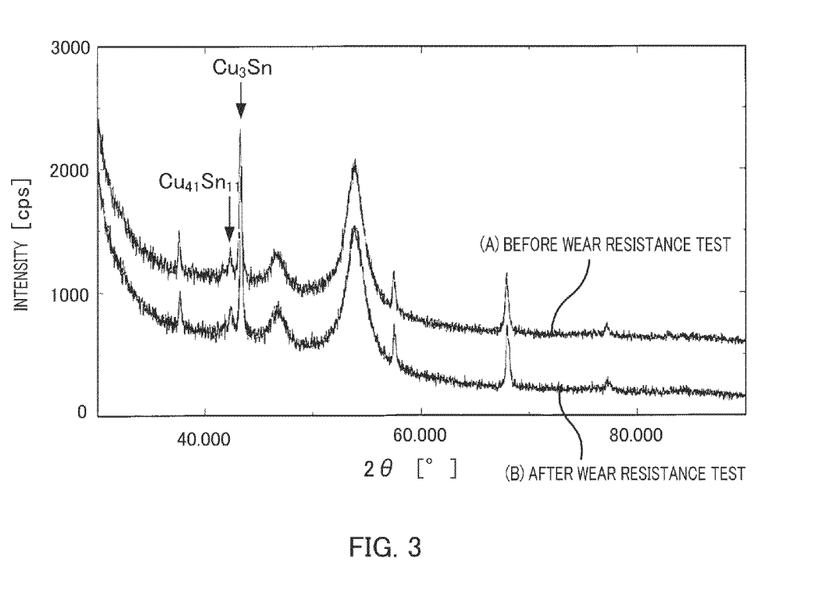
FIG. 3 shows the results of XRD analysis in Example 2.
Figure 4A:
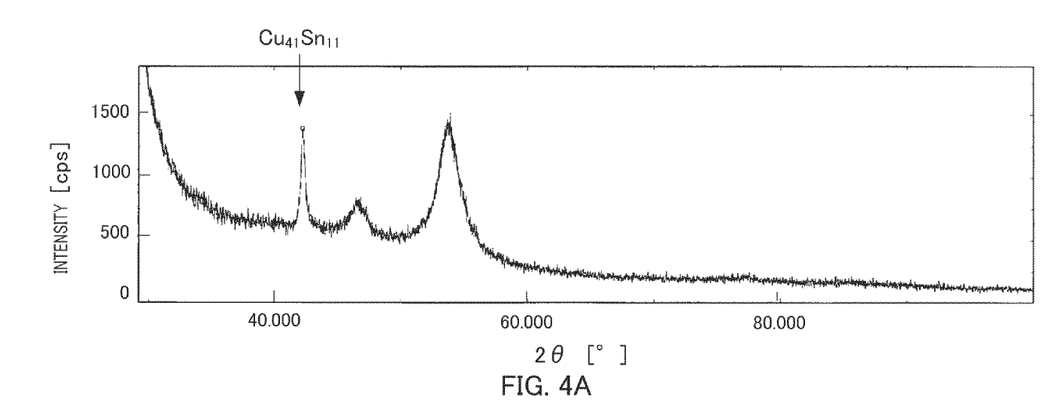
FIG. 4 shows the results of XRD analysis in Comparative Example 1.
Figure 4B:
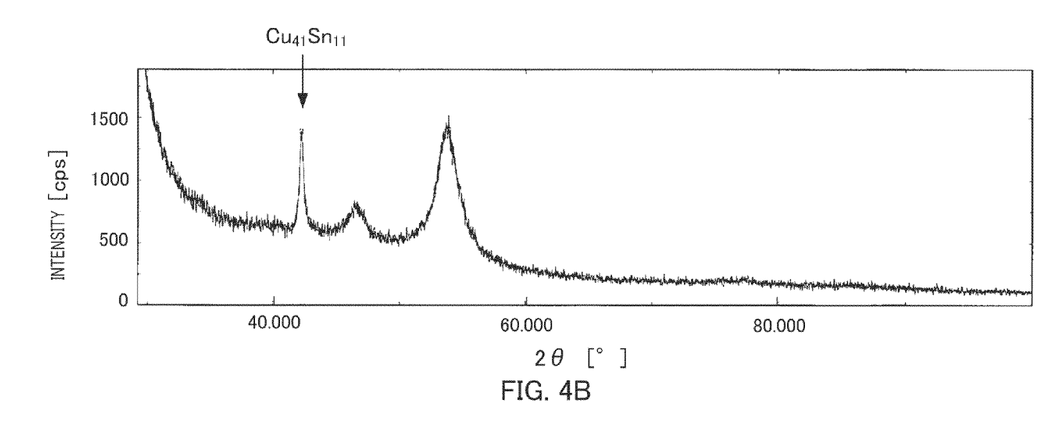

Now, the results of the XRD analysis in FIGS. 2 to 4 are first studied. In the copper-tin alloy layer in Examples 1 and 2, not only a peak ascribed to $Cu_{41}Sn_{11}$ phase, but also a peak ascribed to $Cu_3Sn$ phase were observed (see FIGS. 2 and 3). On the other hand, the peak ascribed to $Cu_{41}Sn_{11}$ phase was observed but the peak ascribed to $Cu_3Sn$ phase was not in the copper-tin alloy layer in Comparative Example 1 (see FIG. 4). It was thus found that the copper-tin alloy layers in Examples 1 and 2 were different from the copper-tin alloy layer in Comparative Example 1 and had $Cu_{41}Sn_{11}$ phase as well as $Cu_3Sn$ phase.

Next, the results of SEM observation in FIGS. 5 to 7 are studied. Few grains were confirmed on the surface of the copper-tin alloy layer in Comparative Example 1 before wear resistance test (see FIG. 7A), whereas grains of moderate size were present at a moderate density (relatively high density) on the surface of the copper-tin alloy layers in Examples 1 and 2 before wear resistance test (see FIGS. 5A and 6A).

It can be seen that while the surface of the copper-tin alloy layer in Comparative Example 1 before wear resistance test had more peeled areas and thus low wear resistance (see FIG. 7B), the surface of the copper-tin alloy layers in Examples 1 and 2 after wear resistance test had less peeled areas and thus high wear resistance (see FIGS. 5B and 6B).

The results shown in FIGS. 2 to 4 and FIGS. 5 to 7 suggest that the copper-tin alloy layers in Examples 1 and 2 has a structure in which moderately sized grains are present at a moderate density and in which an amorphous phase of $Cu_3Sn$ is present among the grains. This structure enables the copper-tin alloy layers in Examples 1 and 2 to lessen the stress induced by friction. In addition, because surface slippage is improved by the presence of grains, the amount of layer peeled off can be reduced in comparison with copper-tin layers with few grains present on the surface. Wear resistance is considered to have been improved by the grains.

Further, it was found that the Q value of the copper-tin alloy layer decreases with increasing amount of $Cu_3Sn$ phase in the copper-tin alloy layer, and increases with increasing amount of $Cu_{41}Sn_{11}$ phase in the copper-tin alloy layer. Thus, it was found that a preferred crystal structure of the copper-tin alloy layer can be expressed in terms of a numerical range of Q value. That is, the copper-tin alloy layers in Examples 1 and 2 whose Q value is in a range of $1.5 \times 10^{-4}$ to $6.0 \times 10^{-4}$ was found to have higher wear resistance than the copper-tin alloy layers in Comparative Examples 1 to 4 whose Q value was not in the above-mentioned range.

Example 3

A copper-tin alloy layer was formed on one side of the above-mentioned nonwoven fabric in the same manner as in Example 1 except that the substrate film was changed to a nonwoven fabric (made of polypropylene, Mitsui Chemicals, Inc., SYNTEX PS-106). The deposition amount of copper-tin alloy was 0.4 mg/mm$^2$. In addition, the ratio of $Cu_{41}Sn_{11}$ crystalline phase to $Cu_3Sn$ crystalline phase, $Cu_{41}Sn_{11}/Cu_3Sn$, was 0.002 as measured by the above-described XRD analysis.

Next, the surface of this nonwoven fabric on which the copper-tin alloy layer was formed was laminated with artificial leather at 120° C. to manufacture a clothing fabric. The clothing fabric was folded into a bag shape and sewed up with the artificial leather outside and the copper-tin alloy layer inside, to manufacture a bag-shaped antimicrobial material (antimicrobial bag).

Example 4

An antimicrobial raw material (antimicrobial woven fabric) was produced in the same manner as in Example 1 except that the substrate film was changed to a nylon clothing fabric (manufactured by NOXA-KURO) and the degree of vacuum of the vapor deposition device was set below $3.0 \times 10^{-3}$ Pa upon deposition of the copper-tin alloy layer. The deposition amount of copper-tin alloy was 0.3 mg/mm². The textile weave of the above nylon clothing fabric was plain weave. In addition, the ratio of $Cu_{41}Sn_{11}$ crystalline phase to $Cu_3Sn$ crystalline phase, $Cu_{41}Sn_{11}/Cu_3Sn$, was 0.002 as measured by the above-described XRD analysis.

Comparative Example 5

For comparison with the antimicrobial bag manufactured in Example 3, a commercially available bag (manufactured by Puma, Ath M2M2ASB type B) was provided. The inner surface of the above-mentioned bag was subjected to antimicrobial and anti-odor treatment (manufactured by Nihon Sanmo, DEW).

Comparative Example 6

For comparison with the antimicrobial woven fabric produced in Example 4, a nylon clothing fabric (manufactured by NOXA-KURO) was provided, wherein the copper-tin alloy layer was not formed on the surface of the nylon clothing fabric.

(Evaluation)

For the bag manufactured in Example 3 and the commercially available bag provided in Comparative Example 5, 9) anti-odor performance test was carried out in the following method. In addition, 10) second antimicrobial performance evaluation was carried out in the following method for the antimicrobial woven fabric produced in Example 4 and the commercially available bag in Comparative Example 5 subjected to the antimicrobial and anti-odor treatment. Furthermore, 11) tensile test and 12) extension performance test were carried out in the following manner for the antimicrobial woven fabric produced in Example 4 and the woven fabric provided in Comparative Example 6.

9) Antiodor Performance Test

An anti-odor performance test was carried out in the following manner for the bag produced in Example 3 and the commercially available bag provided in Comparative Example 5. Medium size T shirts (manufactured by Gunze Limited, THE GUNZE MENS) soaked with 50 mL of sweat were placed separately in the bags produced in Example 3 and the bag provided in Comparative Example 5. The bags were then closed to hermetically-seal the T shirt and allowed to stand for a day at room temperature. A syringe needle was then inserted into the bag and odor inside the bag was collected. For the collected odor, an odor index was calculated using a fragrance analyzer (manufactured by Shimadzu Corporation, FF-2A). The term "odor index" herein refers to a dilution factor when odorous air is diluted with odorless air until the odor becomes unperceivable. Smaller values for dilution factor mean the presence of smaller amounts of odor.

10) Second Antimicrobial Performance Evaluation

For the antimicrobial woven fabric produced in Example 4 and the commercially available in Comparative Example 5 bag subjected to antimicrobial and anti-odor treatment, antimicrobial properties were evaluated in accordance with JIS L1902. Specifically, the number of *Staphylococcus aureus* colonies was counted at the start of bacterial propagation, and 0.5 hours, one hour, two hours, and 18 hours after the start.

11) Tensile Test

The antimicrobial woven fabric produced in Example 4 and the woven fabric provided in Comparative Example 6. The antimicrobial woven fabric produced in Example 4 and the clothing fabric of woven fabric provided in Comparative Example 6 were individually cut in longitudinal and transverse directions into a 15 mm×60 mm piece to prepare samples for evaluation. For these samples, the tension strength of the nylon clothing fabric in a longitudinal direction and transverse direction was measured in accordance with JIS L1096.

12) Extension Performance Test

The antimicrobial woven fabric produced in Example 4 and the clothing fabric of woven fabric provided in Comparative Example 6 were individually cut in longitudinal and transverse directions into a 15 mm×60 mm piece to prepare samples for evaluation. For the samples, % extension of the nylon clothing fabric was measured in accordance with JIS L1096 for longitudinal and transverse directions.

The results of the above 9) anti-odor performance test are shown below.

TABLE 2

|  | Example 3 | Comparative Example 5 | Shirt alone |
|---|---|---|---|
| After one day storage | 18 | 24 | 25 |
| After one week storage | 18 | 22 | 23 |

It is found that the bag produced in Example 3 has a smaller odor index and is excellent in anti-odor performance, as compared with the commercially available bag in Comparative Example 5 subjected to antimicrobial and anti-odor treatment. Further, the antimicrobial bag in Example 3 did not show a significant difference in anti-order performance between after one day storage and after one week storage. This indicates that the antimicrobial bag in Example 3 has a faster rate of anti-odor action.

Figure 8:
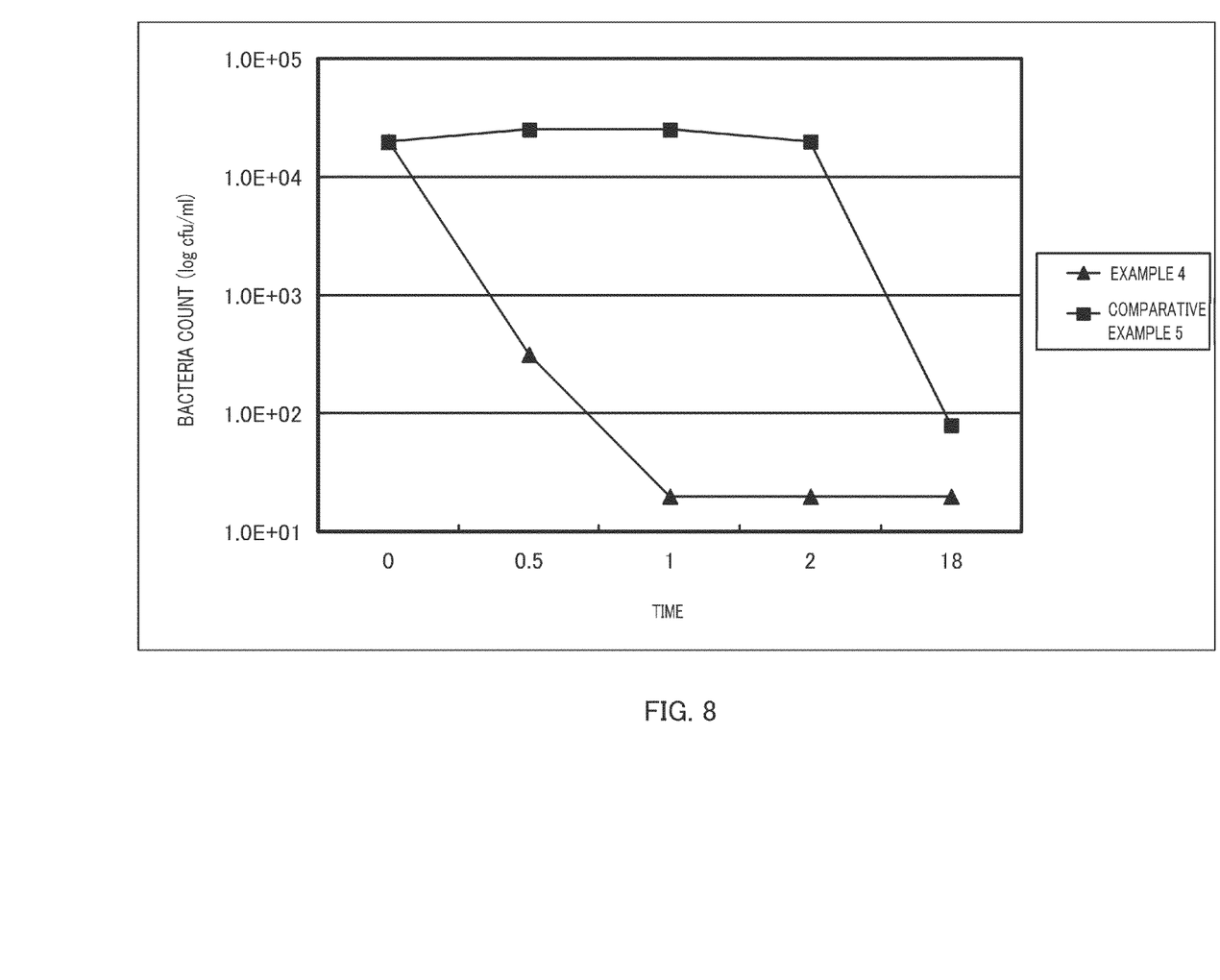
FIG. 8 is a graph of bacteria count vs. time, showing the results of antimicrobial performance evaluation for antimicrobial raw materials (antimicrobial woven fabrics) in Example 4 and Comparative Example 5.

The results obtained by carrying out the 10) antimicrobial performance evaluation 2 were in a graph in FIG. 8. The graph in FIG. 8 shows that antimicrobial woven fabric in Example 4 has higher antimicrobial performance and further a faster rate of decrease in the bacteria as compared with the commercially available antimicrobial bag in Comparative Example 5 subjected to antimicrobial and anti-odor treatment, which bag did not include the copper-tin alloy layer.

The results obtained by carrying out 11) tensile test and 12) extension performance test are shown in Table 3 below.

TABLE 3

|  |  | Example 4 | Comparative Example 6 |
|---|---|---|---|
| Tension strength (N/15 mm) | Longitudinal direction | 190 | 195 |
|  | Transverse direction | 239 | 166 |
| Extension (%) | Longitudinal direction | 23.2 | 29.5 |
|  | Transverse direction | 36.5 | 44.5 |

As seen from Table 3, it was demonstrated that formation of the copper-tin alloy layer according to the present invention on a woven fabric improved tension strength in the transverse direction. Because the textile weave of the clothing fabrics used in Example 4 and Comparative Example 6 is made by plain weaving, i.e., weaving in which transverse threads are woven while applying tension to longitudinal thick threads, the transverse threads are relatively weak. It is considered that formation of the copper-tin alloy layer on this woven fabric allows for close adhesion of the copper-tin alloy among fibers so that high adhesion strength is ensured among the transverse threads thereby improving the tension strength in the transverse direction.

The present application claims priority of JP2011-033669 filed on Feb. 18, 2011 and JP2011-220978 filed on Oct. 5, 2011. The disclosure of which is incorporated herein by reference in their entirety.

Industrial Applicability

The present invention can provide an antimicrobial raw material having high wear resistance as well as high antimicrobial properties and corrosion resistance; a method of producing the same; and an antimicrobial material.

The invention claimed is:

1. An antimicrobial raw material comprising:
    a substrate layer; and
    a copper-tin alloy layer disposed on the substrate layer, the copper-tin alloy layer containing over 60 atomic % to 90 atomic % of copper and 10 atomic % to less than 40 atomic % of tin, wherein
    the copper-tin alloy layer comprises a $Cu_{41}Sn_{11}$ crystalline phase and a $Cu_3Sn$ crystalline phase; and
    a Q value ($\Omega/(nm \cdot Cu$ atomic %)) obtained by dividing a sheet resistance ($\Omega$) of the copper-tin alloy layer by a product of a thickness of the copper-tin alloy layer and a copper content (Cu atomic %) in the copper-tin alloy layer is $1.5 \times 10^{-4}$ to $6.0 \times 10^{-4}$.

2. The antimicrobial raw material according to claim 1, wherein the substrate layer is made of resin, natural fiber or paper, the resin, natural fiber or paper having a temperature under load of 115° C. or below as measured in accordance with ASTM-D648-56 under a load of 1,820 kPa.

3. The antimicrobial raw material according to claim 1, wherein a ratio of the $Cu_{41}Sn_{11}$ crystalline phase to the $Cu_3Sn$ crystalline phase in the copper-tin alloy layer, $Cu_{41}Sn_{11}/Cu_3Sn$, is 0.002 to 0.040.

4. The antimicrobial raw material according to claim 1, wherein a surface roughness Rz of a surface of the copper-tin alloy layer, the surface being remote from the substrate layer, is 14.4 to 15.9 nm.

5. The antimicrobial raw material according to claim 1, wherein the substrate layer is made of polyethylene terephthalate, polyethylene naphthalate, polypropylene, polyethylene, or polyimide.

6. The antimicrobial raw material according to claim 1, wherein the copper-tin alloy layer is formed by simultaneous vapor deposition using an evaporation source composed of a copper-tin alloy containing over 60 atomic % to 85 atomic % of copper and 15 atom % to less than 40 atom % of tin.

7. The antimicrobial raw material according to claim 1, wherein the copper-tin alloy layer covers the entire or part of an outermost surface of the antimicrobial raw material.

8. The antimicrobial raw material according to claim 1, wherein the substrate layer is a nonwoven fabric, woven fabric or yarn.

9. A method of producing the antimicrobial raw material according to claim 1, comprising:
    providing an evaporation source composed of a copper-tin alloy containing over 60 atomic % to 85 atomic % of copper and 15 atom % to less than 40 atom % of tin;
    heating a substrate disposed so as to face the evaporation source; and
    allowing a metal vapor, generated by gasifying the copper-tin alloy from the evaporation source, to contact the substrate heated to form thereon a copper-tin alloy layer.

10. The method of producing the antimicrobial raw material according to claim 9, wherein the heating of the substrate brings a temperature of the substrate to 100 to 125° C.

11. The method of producing the antimicrobial raw material according to claim 9, wherein the substrate is made of resin, natural fiber or paper, the resin, natural fiber or paper having a deflection temperature under load of 115° C. or below as measured in accordance with ASTM-D648-56 under a load of 1,820 kPa.

12. An antimicrobial material comprising the antimicrobial raw material according to claim 1.

13. The antimicrobial material according to claim 12, wherein the antimicrobial material is used as a touch panel protection film.

14. The antimicrobial material according to claim 12, wherein the antimicrobial material is used as medical material.

15. The antimicrobial material according to claim 12, wherein the antimicrobial material is used as purification material.

* * * * *